United States Patent
Le Corre

(10) Patent No.: US 7,783,335 B2
(45) Date of Patent: *Aug. 24, 2010

(54) DEVICE FOR MONITORING ANATOMICAL UNIT OR A RADIOTHERAPY UNIT

(75) Inventor: Patrick Le Corre, Muret (FR)

(73) Assignee: DYN'R, Muret (FR)

( * ) Notice: Subject to any disclaimer, the term of this patent is extended or adjusted under 35 U.S.C. 154(b) by 801 days.

This patent is subject to a terminal disclaimer.

(21) Appl. No.: 10/513,763

(22) PCT Filed: Apr. 22, 2002

(86) PCT No.: PCT/FR02/01371

§ 371 (c)(1),
(2), (4) Date: Aug. 17, 2005

(87) PCT Pub. No.: WO02/085455

PCT Pub. Date: Oct. 31, 2002

(65) Prior Publication Data

US 2006/0129044 A1      Jun. 15, 2006

(30) Foreign Application Priority Data

Apr. 23, 2001 (FR) .................................. 01 05437

(51) Int. Cl.
*A61B 5/05* (2006.01)
(52) U.S. Cl. ..................... 600/407; 600/410; 600/427; 600/428; 600/429; 702/40; 702/57; 702/70; 702/189; 378/65; 378/64
(58) Field of Classification Search ......... 600/427–429, 600/410, 407, 437; 702/40, 57, 70, 189; 378/64, 65
See application file for complete search history.

(56) References Cited

U.S. PATENT DOCUMENTS

| 3,871,360 A | 3/1975 | Van Horn |
| 4,387,722 A | 6/1983 | Kearns |

(Continued)

FOREIGN PATENT DOCUMENTS

DE      19856467      5/2000

(Continued)

*Primary Examiner*—Brian Casler
*Assistant Examiner*—Joel M Lamprecht
(74) *Attorney, Agent, or Firm*—Blakely, Sokoloff, Taylor & Zafman LLP

(57) ABSTRACT

The invention concerns a device for monitoring an imaging or radiotherapy unit (1) for treating members of the human body subject to displacements related to movements of the diaphragm. The invention is characterized in that said monitoring device is designed to enable, in a prior preparation phase, to store two values, called rest value and triggering value, respectively representing, for each patient, of his suspended ventilatory level and an inhalation or exhalation ventilatory level, triggering acquisition of images or irradiation, then, during the real monitoring of the unit (1), in commanding an image or irradiation acquisition, once the correspondence between the measured value of the suspended ventilatory level and the stored rest value has been established, and only when the correspondence between the measured respiratory value of the patient and the stored triggering value has been subsequently established. Additionally, said monitoring device comprises means (11) for displaying the respiratory curve of the patient, which can be viewed by him, and whereon are physically represented the rest and triggering values.

10 Claims, 2 Drawing Sheets

U.S. PATENT DOCUMENTS

| | | | |
|---|---|---|---|
| 4,727,871 A * | 3/1988 | Smargiassi et al. | 128/204.17 |
| 5,038,785 A * | 8/1991 | Blakeley et al. | 600/484 |
| 5,067,494 A * | 11/1991 | Rienmueller et al. | 600/428 |
| 5,414,459 A * | 5/1995 | Bullwinkel | 348/53 |
| 5,751,837 A * | 5/1998 | Watanabe et al. | 382/131 |
| 5,764,723 A | 6/1998 | Amols et al. | |
| 6,690,965 B1 * | 2/2004 | Riaziat et al. | 600/428 |
| 6,959,266 B1 * | 10/2005 | Mostafavi | 702/189 |
| 2003/0055331 A1 * | 3/2003 | Kotmel et al. | 600/410 |
| 2005/0119560 A1 * | 6/2005 | Mostafavi | 600/425 |

FOREIGN PATENT DOCUMENTS

| | | |
|---|---|---|
| FR | 2582500 | 12/1986 |
| WO | WO 98/52635 | 11/1998 |
| WO | WO 99/42034 | 8/1999 |
| WO | WO 99/43260 | 9/1999 |

* cited by examiner

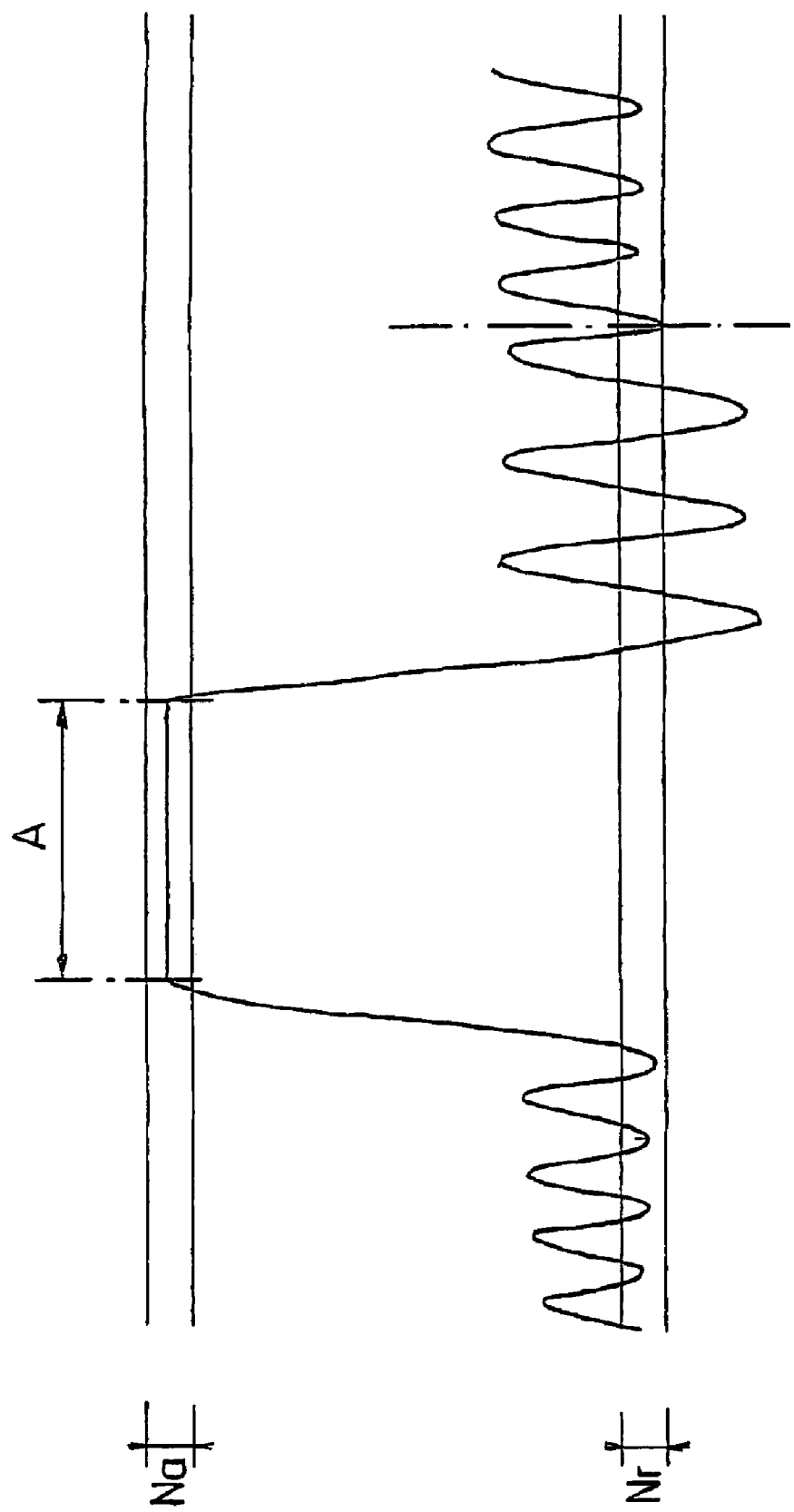

DEVICE FOR MONITORING ANATOMICAL UNIT OR A RADIOTHERAPY UNIT

The invention relates to a device for driving an anatomical imaging unit or a radiotherapy unit for the purpose of treating organs in the human body, and more specifically, organs that are subject to displacements related to the movement of the diaphragm, and the position of which therefore varies as a function of thoracic expansion.

In the field of radiotherapy, x-ray scanners are now integrated into the services, and have resulted in a fundamental transformation of preparation procedures. Helical acquisition has in fact reduced the length of the examination and allowed both a greater number of slices and a low level of reconstruction thickness. These high-quality images have delighted users in respect of both exploration for the purpose of contouring and virtual simulation. The shape of the radiation beams has thus been able to be deduced from the shape of the target volume, and the three-dimensional calculation of the dose distribution has offered analysis tools that favour dosimetric optimization.

Conversely, the precision introduced by the simulation procedure data has made it essential to reduce the daily positioning error. Thus, customized supports made prior to scanner acquisition are now used during the preparation procedure and at all treatment sessions. In spite of that, assessments have nonetheless demonstrated the limitations of daily precision and have led to the adoption of margins adapted to each situation.

It is more difficult, on the other hand, to take account of diaphragm movements and therefore of the organ to be displayed and treated between the different preparation phases and at each treatment session. Of all the sources of mobility, in fact, breathing causes the most significant disruption. The most significant displacements, as has been shown by a number of studies, are found near the diaphragm and may reach as much as 4 cm, and are therefore far in excess of the daily repositioning error.

In order to find a solution to this problem it has been envisaged to evaluate the ranges of movement of the organs with breathing, and to incorporate these ranges in the dosimetric plan. However, it has seemed unrealistic to apply corresponding margins without running the risk of creating major complications, for example in the lungs when treating thoracic tumours, and of compromising the quality of patient care.

To this data it should be added that the quality of the treatment also depends on the skill of the operators who are not always necessarily the same during a series of treatment sessions.

In practice, it follows from what has been said above that the potentialities related to virtual simulation are not exploited in an optimum way, and that, in the context of radiotherapy, radiation doses are currently of necessity relatively small, and cases of therapeutic complications, such as radiation-induced lung diseases during the treatment of thoracic tumours, unfortunately still far too numerous.

The purpose of the present invention is to overcome the above-mentioned drawbacks of anatomical imaging and radiotherapy and its main purpose is to provide a drive device that can bring about a significant reduction in the geometrical margins as currently introduced, and thereby allow clear and accurate reconstructions in three dimensions, can almost eliminate the risks of complications such as radiation-induced lung diseases, and allow the doses administered to be increased.

A further objective of the invention is to provide a device that allows patients to take responsibility for themselves and to experience the treatment sessions in a calmer frame of mind.

Another objective of the invention is to provide a device that consists of a very "light" piece of equipment with a low cost price and small space requirement, which is very easy to employ.

Another objective of the invention is to provide a device that allows image acquisition or radiation triggering to be controlled automatically.

To this end, the invention applies to an anatomical imaging or radiotherapy unit drive device, comprising:
  means for measuring the thoracic expansion of patients,
  a control unit connected to measurement means so as to receive signals emitted by them, and to the imaging or radiotherapy unit so as to drive it, said control unit:
  comprising means for storing so-called resting and trigger values, representing respectively, for each patient, his level of resting ventilation and an inhalation or exhalation respiratory level, for triggering image acquisition or radiation,
  being programmed so as to control an image acquisition or radiation, once the correspondence is established between the measured value of the resting ventilation level and the stored resting value, then only when the correspondence is subsequently established between the measured value of the patient's respiratory level and the stored trigger value, and so as to stop the acquisition or radiation when this second correspondence is no longer respected,
  and means for viewing the patient's breathing curve that are connected to the control unit and placed so as to be viewable by said patient, said control unit being adapted so as to generate the display on said viewing means of the resting values and trigger values.

Such a drive device is therefore designed to be able to operate in the following way:
  in a prior preparation phase:
    the patient's current metabolic volume is measured, and a value, known as the resting value, and representing his resting ventilation level, is stored
    and when the patient is in resting respiratory conditions, he is asked to inhale or exhale, the respiratory level is determined for which the acquisition or radiation will be triggered, and a value, known as the trigger value and representing this respiratory level, is stored
  and at each treatment session, or at each subsequent imaging session intended for example to allow the effects of a treatment to be monitored, the patient's respiratory level is continuously measured and:
    when the patient is at rest, his resting ventilation level is compared with the stored resting value,
    when there is a correspondence between the measured and stored resting values, a radiograph acquisition or radiation sequence is initiated consisting in authorising triggering only when the patient has stopped his breathing at a respiratory level corresponding to the stored trigger value and in bringing it to an end when the patient ceases to hold his breath,
    and the resting/trigger cycles are repeated until the scheduled radiation time for the session has elapsed, or until all the radiographs required have been made.

The device according to the invention therefore allows, in a prior phase, two values to be stored representing respectively the patient's resting ventilation level, and the pulmonary volume when inhaling or exhaling of the patient, in respect of whom it has been decided to trigger the radiography or radiation.

Subsequently, at each imaging or treatment session, triggering is only initiated if the patient, previously in a situation of breathing at rest, has managed to stop his breathing at the required breathing trigger level.

Triggering therefore only occurs when the following two conditions are met: an initial condition which makes it essential for the patient to breathe normally before holding his breath, and a final condition which makes it essential that the breath is held with a level of breathing that is always identical both at each radiograph acquisition session and at one and the same treatment session, and from one treatment session to another.

The necessity of meeting these two conditions, together with the fact that the two values calculated in the previous imaging phase are stored in a patient dedicated file, means the achievement of complete reproducibility of the apnoea conditions and complete repetitivity of radiation or complete similarity of the conditions in which the successive radiographs are taken.

In practice, and in the first place, the fact that all the radiographs are taken in strictly identical conditions of breath holding, leads to very accurate and very clear reconstructions in three dimensions, which allow the theoretical margins introduced during the reconstructions to be reduced.

Moreover, at radiotherapy sessions, the fact that the radiation is applied when the patient is holding his breath in other words when the organ to be treated is not subject to any movement resulting from breathing, together with the perfect reproducibility of these apnoea conditions, also allows the theoretical margins introduced to take account of respiratory movements to be significantly reduced.

It should be noted that the pure and simple elimination of these theoretical margins may occur if it is decided not to take account of transverse cardiac movements or any thoracic relaxation. On the assumption that these elements are taken into account, it means that these theoretical margins may be reduced to values of about 2 to 3 mm, in the treatment of thoracic tumours.

The result of the above-mentioned advantages relating to the invention is that the device according to the invention leads to a new situation where the risk of therapeutic complications can be reduced to the point of no longer presenting an obstacle to plans to increase doses.

Furthermore, and in an essential way, once the prior preparation phase is implemented, and at each subsequent session, the patient is able to view his respiratory curve on which the stored resting and trigger values are embodied. This viewing by the patients of their respiratory curve in fact allows them to take responsibility for and to involve themselves in controlling the level of apnoea. In practice, taking responsibility in this way tends to make the patients much more attentive and calmer.

Moreover, with regard to this calmness, it should be noted that the patient alone is in control of the moment when he will trigger his apnoea, from the moment when he is breathing normally. As a consequence, he is able to conduct each session at his own pace, without any stress.

It should be noted, additionally, that this involvement of the patients constitutes one of the basic principles for operating the drive device according to the invention, since it authorises, without any danger of stress for these patients given that they themselves are managing the operation of the sessions, the triggering of these radiograph acquisition or radiation sessions, for ventilation levels in excess of the resting ventilation level.

Because of this, in fact, practitioners benefit, in respect of each patient, from a wide range of respiratory levels in determining a positioning of the target-volume that allows optimum acquisition and treatment in perfectly reproducible conditions.

It should be noted, in this regard, that it has already been envisaged, as described in documents WO 98/52635 and U.S. Pat. No. 5,067,494, to trigger the radiation of a target-volume when the patient is in a position of holding his breath at a given respiratory level.

However, current devices for implementing this principle consist of very cumbersome pieces of equipment, such as the artificial respiration unit described in WO 98/52635.

Moreover and above all, the technique employed still consists in using a closed respiratory circuit which leaves the initiative for stopping the patients breathing for the purpose of radiation to the operator alone.

For this reason, and in the first place, perfect reproducibility of the trigger conditions cannot be guaranteed given the fact that it depends on operator involvement.

Moreover, since trigger management is incumbent on the operator alone, these triggers can only be prompted at respiratory levels comparable to the resting respiratory level, in the absence of which patients could not withstand full treatment sessions.

According to one advantageous embodiment, the means for measuring thoracic expansion include a spirometer. The spirometer is, indeed, the only measurement means that makes it possible to provide a correlation between thoracic expansion and the corresponding volume of air.

Moreover, the control unit advantageously includes, for each patient, means of storing a trigger value representing an inhalation level. In fact an inhalation phase apnoea, leading to the lungs increasing in size and to a reduction in their density, has also proved to bring about a reduction in the target volume which helps protect the lung when treating thoracic tumours. Moreover, inhalation also causes a reduction in the pulmonary tissue and consequently the risks of lesions through the irradiation of healthy tissue surrounding the target volume.

Additionally, increasing the volume of the lungs is salutary for the numerous patients breathing inadequately on account of their tobacco addiction, since for some it may constitute a source of success in their radiotherapy.

Moreover, and to advantage, according to the invention, the drive device includes support means for the spirometer that are able to keep it in a withdrawn position relative to the patient's head, said spirometer being connected to an oral nozzle via a breathing tube on which is interposed an interchangeable bacterial filter.

This positioning of the spirometer allows the patient to stretch out in the dorsal decubitus position, with his hands crossed on top of his head, so that the thorax of this patient is totally disengaged, thus allowing the positioning of oblique beams. Moreover, the interchangeable bacterial filter is intended to avoid any risk of contamination between patients.

According to one advantageous embodiment, the control unit comprises means for storing a range of resting and trigger values, each representing a measurement margin relative to the measured resting and trigger values.

The objective of this measurement margin is to take account of possible variations in the resting ventilation level and apnoea level which can be estimated at about 5% of the vital capacity for a stoppage in deep inhalation.

According to another advantageous embodiment which may or may not be added to the one mentioned before, the control unit is programmed, with view to controlling an acquisition or radiation, so as to measure in real-time the actual values of the patient's resting ventilation level and to calculate at each moment, as a function of the measured resting value, a trigger value redefined relative to said resting value.

According to this embodiment the trigger value at a moment t is systematically redefined relative to the resting value measured at a moment t-ϵ, therefore a real resting value, and the drive device is therefore then designed so as to take account of possible drifts of the resting ventilation level, resulting for example from variations in temperature, humidity etc.

Furthermore, and to advantage, the control unit is programmed so as to authorise the triggering of the acquisition or radiation after a pre-set lapse of time following the moment when the correspondence is established between the stored and measured trigger values. The purpose of this time lapse is to make sure that the patient fully maintains his apnoea, in order particularly to avoid an untimely triggering. It also makes it possible to take account of either the inertia of the imaging or radiotherapy unit, or the operator response time.

Furthermore, the drive device includes to advantage means for viewing the patient's respiratory curve connected to the control unit and placed so as to be viewable by the operator, and means for communicating between the operator and the patient that are able to allow said patient to be informed of the moment when the measured and stored resting values correspond.

These viewing means allow the operator to check the proper operation of the session and to inform the patient, after each apnoea, of the moment from which he recommence his apnoea.

To advantage, the communication means include, additionally, a control button to switch on a light on the patient's viewing means.

Furthermore, for the purposes of automation and eliminating any risk of human error, and to advantage, the control unit is programmed so as to activate the imaging or radiotherapy unit automatically when there is a correspondence between the measured and stored trigger values.

However, for the purposes of security, and to advantage, the drive unit includes an intermediary housing interposed between the control unit and the imaging or radiotherapy unit, and comprising an emergency stop button that can be activated by an operator.

Other characteristics, purposes and advantages of the invention will emerge from the following detailed description with reference to the appended drawings which show a preferential embodiment thereof as a non-restrictive example. In these drawings:

FIG. 2 is a graph showing the respiratory curve of a patient undergoing treatment, as shown to said patient and to the operator.

Figure 1:
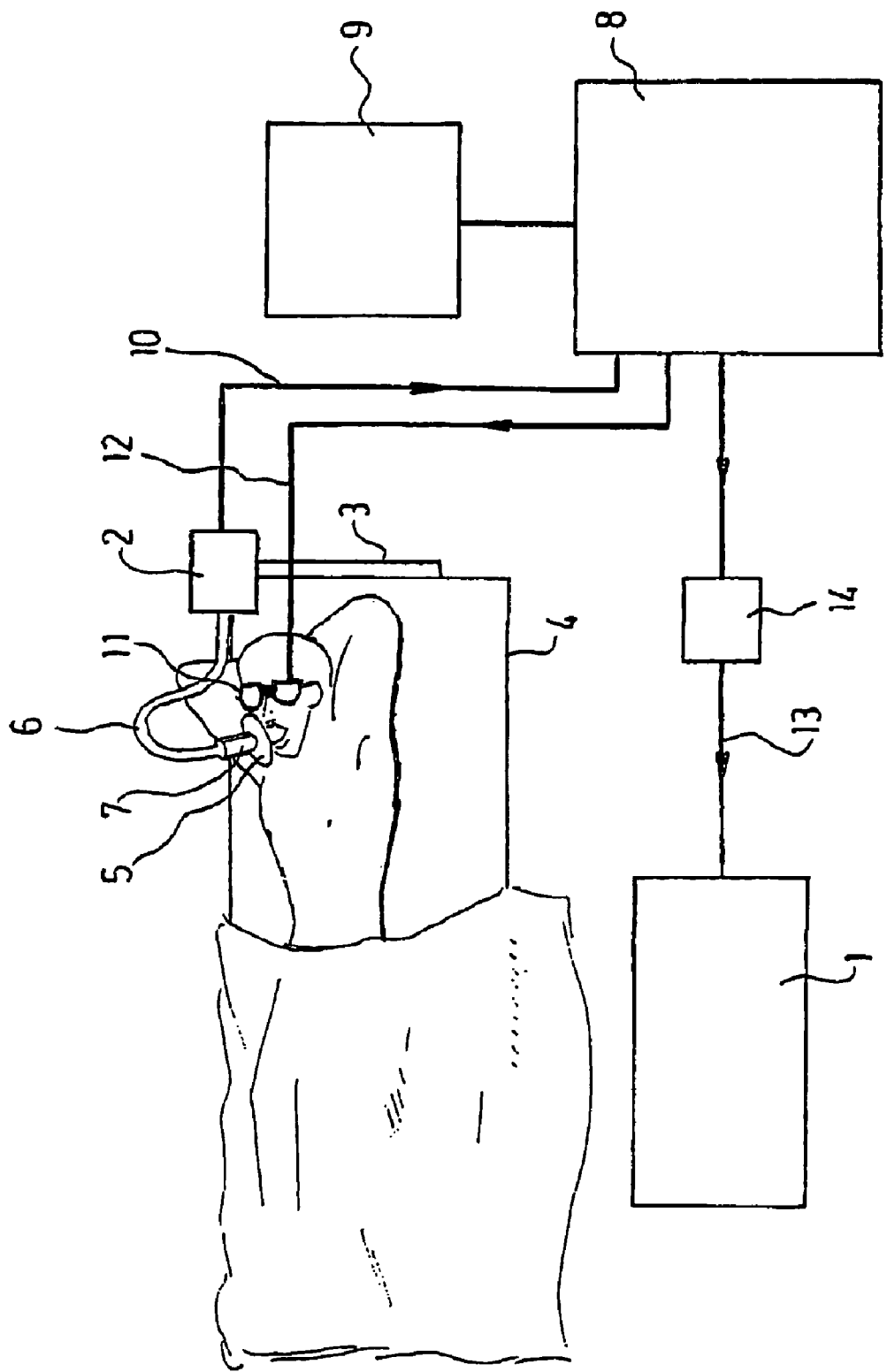
FIG. 1 is a block diagram of a drive device in accordance with the invention.

The device shown by way of example in FIG. 1 is adapted to drive a radiotherapy unit 1 intended for the treatment of thoracic tumours and comprising a particle accelerator.

This drive device comprises, in the first place, a spirometer 2 of the pneumo-tachograph type comprising a respiratory flow differential pressure sensor integrator, and adapted to deliver an electrical signal representing the volume of air corresponding to the thoracic expansion.

This spirometer 2 is fixed via any means 3 known per se to the head of the treatment table 4 so as to be positioned beyond the head of the patient during preparation and treatment sessions.

This arrangement makes it possible, in fact, as shown in FIG. 1, for the patient to stretch out in the dorsal decubitus position with his hands crossed on top of his head, in other words in a position that totally disengages the thorax, allowing the positioning of oblique beams.

The spirometer 2 is additionally connected to an oral nozzle 5 via a flexible pipe 6 on which is interposed an interchangeable bacterial filter 7.

The spirometer 2 additionally incorporates means for heating the sensor to a stabilised temperature, such as an electrical resistance, kept permanently supplied with power during the preparation and treatment sessions and intended to eliminate the humidity produced by the patient's breathing which may cause errors in the value of the calculated volumes due to the modification of the characteristics of the element constituting the drop in pressure.

Moreover, since this spirometer is dedicated to radiotherapy (or to imaging), it is not possible to disconnect the patient during the session, with a view to setting, with each new measurement, and as is required by any conventional spirometer, the differential pressure integrator to zero. The spirometer according to the invention is therefore equipped with a specific system, such as a bypass circuit that can be controlled by the operator, and which allows the differential pressure integrator to be isolated during each zero flow reading.

The device additionally includes a micro-computer 8 to which a monitor 9 is connected. This micro-computer 8, placed in proximity to the control console is connected to the spirometer 2 via a connection 10, so as to receive a signal representing the patient's respiratory curve as a function of the time which can be viewed on the monitor 9.

The device additionally includes a pair of goggles 11 comprising at least one liquid crystal screen, connected by a cable 12 to an interface output of the micro-computer 8, and intended to be worn the patient so as to allow him to view his respiratory curve.

The device comprises finally a control connection 13 connecting the micro-computer 8 and the radiotherapy unit 1 allowing the latter to be controlled automatically. On this link 13 is additionally interposed an intermediary housing 14 intended to be placed in proximity to the control console, and comprising an emergency stop button and a power on/off light allowing the operator to verify that operations are proceeding normally.

Radiotherapy treatments using the drive device according to the invention take place as described below.

In the first place, the radiotherapy preparation procedure comprises, prior to any examination, the making of a customised hemi-corporal support in polyurethane foam.

Throughout the preparation and treatment stages described hereinafter, the patient, placed in his support is stretched out on the treatment table 4 in the dorsal decubitus position, with his hands crossed on top of his head, so as to disengage the totality of the thorax. Moreover, he is taken care of by the radiotherapy dedicated scanner.

Furthermore prior to any preparatory or treatment session, the spirometer 2 is calibrated so as to guarantee the reproducibility of the values measured from one session to another.

The first preparation stage, apart from the conventional stages of contouring the target volume and determining the radiation beams and, generally, the treatment to be administered, also consists in determining and storing two values which will condition the operation of the treatment sessions.

The first value is determined when the patient breathes normally, at rest, by measuring his current metabolic volume, and storing a resting value Nr representing the resting ventilation level of this patient.

The second value is, for its part, determined when the patient inhales deeply, by raising the level of inhalation in respect of which the tumour is located in an optimum position for radiograph acquisition and radiotherapy treatment. The corresponding stored value called the trigger value Na level corresponds to the inhalation level in respect of which radiograph acquisition and radiation will subsequently be triggered at all sessions.

The values are additionally stored with a measurement margin that is parameterisable as a function of the breathing capacity of the patients, this measurement margin being intended to make it possible to take account of any variations in the resting ventilation and apnoea level.

Furthermore a patient dedicated file, intended to integrate all treatment related parameters and data with a view to ensuring perfect traceability, is used for storage.

Once the preparation stage has been implemented, and at all treatment sessions, the control unit is programmed to continuously calculate the patient's respiratory curve as a function of the signal delivered by the spirometer 2 and to display a graphical representation of this curve on the screens of the monitor 9 and the goggles 11.

Furthermore, as shown in FIG. 2 the resting Nr and trigger Na values are also displayed on the screens with their measurement margin.

At each session, when the patient's breathing is normal, in other words when his resting ventilation level coincides with the resting value, said patient is informed by the operator, for example by switching on a light, for example a green light, on the screens of the goggles 11, that he may trigger an apnoea.

From this moment on, the patient is able to take full responsibility and to trigger this apnoea when he so wishes. Moreover since he can see his respiratory curve in front of him this patient is easily able to control his apnoea level so that it coincides with the trigger value Na.

Once this level of apnoea is obtained and after stabilisation for a period of about 1 s, the control unit 8 is programmed to trigger radiation for a length of time corresponding to the time during which the patient maintains his apnoea or for a period of time set by the operator at the end of which a light, for example a red light, is switched on on the screens of the goggles 11. The patient is then able to resume his normal breathing so that his resting ventilation level once again coincides with the resting value Nr.

According to the invention device, the radiotherapy unit 1 is therefore driven automatically with remarkable repetitivity and reproducibility of levels of shot and the patient, who is involved in the sessions, experiences them in a much calmer frame of mind.

The invention claimed is:

1. A device for driving a radiotherapy unit for the purpose of treating organs in the human body subject to displacements related to movements of the diaphragm comprising:
    a spirometer for measuring the pulmonary volume of patients,
    support means for the spirometer that are able to keep it in a withdrawn position relative to the patient's head, said spirometer being connected to an oral nozzle via a breathing tube on which is interposed an interchangeable bacterial filter,
    a control unit connected to the spirometer, and to the radiotherapy unit so as to drive it, said control unit comprising:
        means for storing so-called resting and trigger values, representing respectively, for each patient, his level of resting ventilation and an inhalation or exhalation respiratory level,
        means for viewing the patient's breathing curve that are connected to the control unit and placed so as to be viewable by said patient, said control unit being adapted so as to generate the display on said viewing means of the resting and trigger values,
        said control unit being programmed so as to perform the following steps:
            when a patient is breathing at rest, the value of the patient's respiratory level measured by the spirometer is compared with the stored resting value,
            only when a first correspondence is established between the measured value of the patient's respiratory level and the stored resting value, the patient is subsequently asked to initiate a voluntary apnea which level is controlled by the patient himself by viewing his breathing curve on said means for viewing, so that a radiation session is initiated consisting of:
                when the patient is performing said voluntary apnea, radiation is triggered immediately by the control unit only when a second correspondence is established between the measured value of the patient's respiratory level and the stored trigger value, and
                said radiation is terminated immediately by the control unit when the patient ceases his voluntary apnea with this second correspondence being no longer respected.

2. The drive device according to one of claim 1, wherein the viewing means consist of goggles equipped with at least one liquid crystal screen.

3. The drive device according to claim 1, wherein the control unit includes, for each patient, means for storing a trigger value representing an inhalation level.

4. The drive device according to claim 1, wherein the control unit comprises means for storing a range of resting trigger values, each representing a measurement margin relative to the measured resting and trigger values.

5. The drive device according to claim 1, wherein the control unit is programmed, for the purpose of controlling an acquisition or radiation, so as to measure in real-time the actual values of the patient's resting ventilation level and to calculate at each moment, as a function of the measured resting value, a trigger value redefined relative to said resting value.

6. The drive device according to claim 1, wherein the control unit is programmed so as to authorize the triggering of the acquisition or radiation after a pre-set lapse of time following the moment when the correspondence is established between the stored and measured trigger values.

7. The drive device according to claim 1, comprising a means for viewing the patients respiratory curve connected to the control unit and placed so as to be viewable by the operator, and means for communicating between the operator and the patient that are able to allow said patient to be informed of the moment when the measured and stored resting values correspond.

8. The drive device according to claim 1, wherein the communication means include a control button to switch on a light on the patient's viewing means.

9. The drive device according to claim 1, wherein the control unit is programmed so as to activate the imaging or radiotherapy unit automatically when there is a correspondence between the measured and stored trigger values.

10. The drive device according to claim 1, comprising an intermediary housing interposed between the control unit and the imaging or radiotherapy unit, and comprising an emergency stop button that can be activated by an operator.

* * * * *